United States Patent [19]
Gilli

[11] Patent Number: 4,869,252
[45] Date of Patent: Sep. 26, 1989

[54] APPARATUS AND METHOD FOR CONTROLLING PULSE ENERGY IN ANTITACHYARRHYTHMIA AND BRADYCARDIA PACING DEVICE

[75] Inventor: Norma L. Gilli, Littletown, Colo.

[73] Assignee: Telectronics N.V., Netherlands Antilles

[21] Appl. No.: 142,535

[22] Filed: Jan. 11, 1988

[51] Int. Cl.[4] .................. A61N 1/00; H05G 00/00
[52] U.S. Cl. .................. 128/419 PG; 128/419 D
[58] Field of Search .................. 128/419 D, 419 PG

[56] References Cited

U.S. PATENT DOCUMENTS

| | | | |
|---|---|---|---|
| 3,857,398 | 12/1974 | Rubin | 128/419 D |
| 3,952,750 | 4/1976 | Mirowski et al. | 128/419 D |
| 4,181,133 | 1/1980 | Kolenik et al. | 128/419 D |
| 4,403,614 | 9/1983 | Engle et al. | 128/419 D |
| 4,473,078 | 9/1984 | Angel | 128/419 PG |
| 4,577,633 | 3/1986 | Berkovits et al. | 128/419 PG |
| 4,693,253 | 9/1987 | Adams | 128/419 D |

OTHER PUBLICATIONS

L. Rubin et al., "Pacing Thresholds Immediately After Defibrillation", Abstract 0654, *Circulation*, vol. 53 and 54, Supp. II, Oct. 1976.

L. Rubin et al., "Effect of Defibrillation Energy on Pacing Threshold", *Medical Instrumentation*, vol. 17, No. 1, pp. 15-17 Jan-Feb, 1983.

R. Yee et al., "Pacing Threshold Chnages after Transvenous Catheter Counter-shock", *American Journal Cardiology*, vol. 53, pp. 503-507, (Feb. 1984).

Primary Examiner—Francis Jaworski
Assistant Examiner—George Manuel
Attorney, Agent, or Firm—Gottlieb, Rackman & Reisman

[57] ABSTRACT

An apparatus and method for controlling pulse energy in an arrythmia control device wherein bradycardia pacing pulses are normally delivered at a first energy, and after antitachycardia therapy, bradycardia pulses are delivered at a second energy, the second energy being greater than the first energy. The antitachycardia therapy may be at least one of antitachycardia pacing, cardioversion and defibrillation; and is delivered at a third energy level greater than said second energy level. The second energy level is maintained for a predetermined period of time and then returned to the normal bradycardia pacing energy.

29 Claims, 5 Drawing Sheets

APPARATUS AND METHOD FOR CONTROLLING PULSE ENERGY IN ANTITACHYARRHYTHMIA AND BRADYCARDIA PACING DEVICE

TECHNICAL FIELD

This invention relates to implantable medical devices which deliver electrical energy to cardiac tissue in an attempt to revert tachycardia and restore a normal sinus rhythm, and more particularly to such devices which exhibit multiple pacing energy levels.

As used herein, antitachycardia pacing will mean any pacing for the reversion of tachycardia. Tachycardia refers to any fast abnormal rhythm of the heart which may be amenable to electrical discharges and specifically includes ventricular tachycardia (VT), supraventricular tachycardia (SVT), ventricular flutter and/or ventricular fibrillation (VF).

The term therapy as used herein includes the processes used between the detection and reversion of a tachyarrhythmia and includes the actions of antitachycardia pacing, cardioversion and/or defibrillation shocks. The term cardioversion refers to the discharge of electrical energy into the cardiac tissue in an attempt to terminate or revert a tachyarrhythmia. This may take the form of a high energy discharge (up to 40 Joules or more) or a low energy discharge (less than 1 Joule). Cardioversion shocks may or may not be synchronized to the rhythm of the heart. Defibrillation is a particular example of cardioversion.

This invention applies equally to devices which deliver energy synchronized to an R-wave and to those that do not, and applies to devices which use lower energy pulses (up to 1 Joule) as well as to devices which use higher energy pulses (up to 40 Joules or more). The invention applies to devices which deliver cardioverting shocks alone as well as to devices which deliver antitachycardia pacing pulses alone or in combination with cardioverting shocks. The invention will usually apply to ventricular implantable cardioverters, but is equally applicable to atrial cardioverters or multiple chamber cardioverters or defibrillators. The invention applies also to the delivery of any antitachycardia pacing pulse and post reversion pacing therapy.

BACKGROUND ART

Many advances are being made in the development of devices and techniques for providing effective medical responses to a variety of heart disorders or arrhythmias. Recent efforts have resulted in the development of implantable cardioverting and pacing devices. One example of such a cardioverting device is disclosed in U.S. Pat. No. 3,952,750 to Mirowski et al.

Despite recent advances there is still room for improvement in this field of implantable devices. There has been an increasing recognition of the need for a device which provides comprehensive automatic control of various cardiac arrhythmias, including ventricular bradycardia, ventricular tachycardia, and ventricular fibrillation.

U.S. Pat. No. 3,857,398 to Rubin is typical of the prior art. It discloses an implantable device which combines pacemaker and defibrillation functions. The device utilizes separate circuitries in dealing with the different functions of pacing and defibrillation. Rubin makes no mention of changing the energy of the pacing pulses. All pacing pulses apparently have the same energy.

U.S. Pat. No. 4,181,133 to Kolenik et. al. discloses an apparatus which provides cardiac pacing and tachycardia break-up pulses. At the onset of tachycardia, the tachycardia pacing pulses are generated and delivered through an output circuit utilized commonly with demand pacer circuitry. Thus, the tachycardia pacing pulses are programmed with the same pulse width and amplitude as the bradycardia pacing pulses.

DISCLOSURE OF THE INVENTION

An existing problem with these antitachyarrhythmia devices is the inability to consistently capture during antitachycardia pacing. It has been found that pulses which have under bradycardia conditions been able to gain capture, have under tachycardia conditions, been unable to gain capture. This may be because the heart has just been traumatized by the VT or VF episode. In these situations it has been found that higher energy pulses are necessary to ensure capture during antitachycardia pacing. The higher energy pulses could be of higher amplitude, greater pulse width or a combination of these factors. It has also been found that after antitachycardia pacing or defibrillation shock therapy, the heart is still in a state of trauma following the VT/VF or the defibrillation shock. Furthermore, the refractory period also changes, and this results in a corresponding change in the capture threshold. Hence, in order to ensure capture, it is necessary for the post therapy bradycardia pacing pulses to have a higher energy than the normal bradycardia pacing pulses. Again, this form of energy is programmed to consist of a higher amplitude, greater pulse width or a combination of these factors.

During antitachycardia pacing, pulses which have under bradycardia conditions captured, suddenly no longer capture. Similarly, after a patient has received a defibrillation or cardioversion shock, there may be an immediate loss of capture as a result of an increase in the capture threshold level. In accordance with the principles of my invention, pulse amplitude and/or pulse width are automatically increased when tachycardia has been detected, and post reversion pulse width and/or amplitude remains high for a predetermined time interval (which interval may be made a programmable parameter).

In accordance with the invention, an apparatus for treating cardiac arrhythmias comprises means for delivering bradycardia pacing pulses, means for the detection of tachycardia, means for delivering antitachycardia pacing pulses from the time of said tachycardia detection wherein said antitachycardia pacing pulses have a higher energy relative to said bradycardia pacing pulses.

Also, in accordance with the invention, an apparatus for treating cardiac arrhythmias comprises means for delivering bradycardia pacing pulses, means for the detection of tachycardia, means for delivering antitachycardia therapy after onset of said tachycardia detection, means for reconfirmation of the absence of tachycardia following the delivery of said antitachycardia therapy and means for delivering post reversion bradycardia pacing pulses for a pre-determined time period wherein said post reversion bradycardia pacing pulses are of a higher energy than said bradycardia pacing pulses delivered prior to the onset of said tachycardia.

The invention further includes a method for treating cardiac arrhythmias and of operating a tachycardia reversion device comprising the steps of delivering bradycardia pacing pulses, detecting the presence of tachycardia, and delivering antitachycardia pacing pulses from the time of said tachycardia detection wherein said antitachycardia pacing pulses have a higher energy than the preceding bradycardia pacing pulses.

Additionally, the invention provides a method for treating cardiac arrhythmias and of operating a tachycardia reversion device comprising the steps of delivering bradycardia pacing pulses, detecting the presence of tachycardia, delivering antitachycardia therapy after the onset of said tachycardia detection, reconfirming the absence of tachycardia following the delivery of said antitachycardia therapy, and delivering post reversion bradycardia pacing pulses for a pre-determined time period wherein said post reversion bradycardia pacing pulses are of a higher energy than said bradycardia pacing pulses delivered prior to the onset of said tachycardia.

Thus, it is an object of the present invention to provide an apparatus and a method for treating cardiac arrythmias which assures capture of the heart after antitachycardia therapy.

It is a further object of the invention to provide an apparatus and method for treating cardiac arrhythmias which provides bradycardia pacing, antitachycardia therapy and defibrillation when needed.

BRIEF DESCRIPTION OF THE DRAWINGS

Further objects, features and advantages of the invention will become apparent upon consideration of the following detailed description in conjunction with the drawings, in which.

BEST MODE FOR CARRYING OUT THE INVENTION

Figure 1:
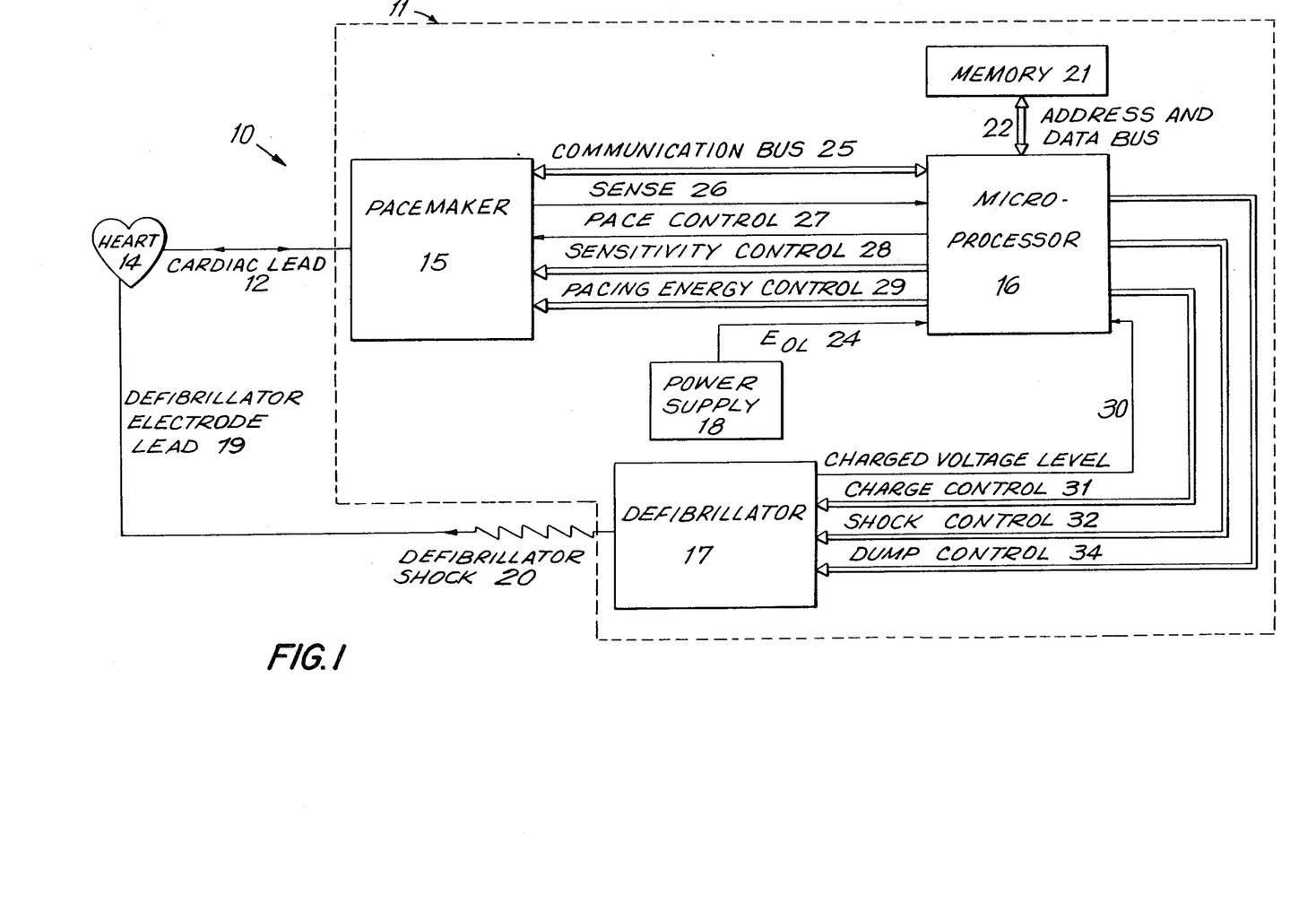
FIG. 1 is a block diagram of an arrhythmia control system in which the present invention may be used.

Referring to FIG. 1, there is depicted a block diagram of an arrhythmia control system 10. System 10 is designed to be implantable and includes a pulse module 11 and appropriate leads. More particularly, system 10 will generally include: a cardiac lead 12 connected to the patient's heart 14; a pacemaker 15 for the detection of analog signals representing cardiac electrical activity and for the delivery of pacing pulses to the heart; a microprocessor 16 which, in response to various inputs received from the pacemaker 15 as well as from a defibrillator 17, performs various operations so as to generate different control and data outputs to both pacemaker 15 and defibrillator 17; and a power supply 18 for the provision of a reliable voltage level to pacemaker 15, microprocessor 16 and defibrillator 17 by suitable electrical conductors (not shown). Defibrillator 17 produces a high voltage to charge its capacitors and then discharges them in response to control signals from microprocessor 16. A defibrillator electrode lead 19 transfers the energy of a defibrillator shock 20 from the implanted pulse module to the surface of the heart 14.

Microprocessor 16 is connected to an external memory 21 by an address and data bus 22. An end-of-life (EOL) signal line 24 is used to provide, to microprocessor 16, a logic signal indicative of the approach of battery failure in power supply 18.

As more fully described below, microprocessor 16 and pacemaker 15 are connected by a communication bus 25, a sense line 26, a pace control line 27, a sensitivity control bus 28, and a pacing energy control 29. As also more fully described below, microprocessor 16 is connected to defibrillator 17 by a charge level line 30, a charge control bus 31, a shock control bus 32, and a dump control bus 34.

Figure 2:
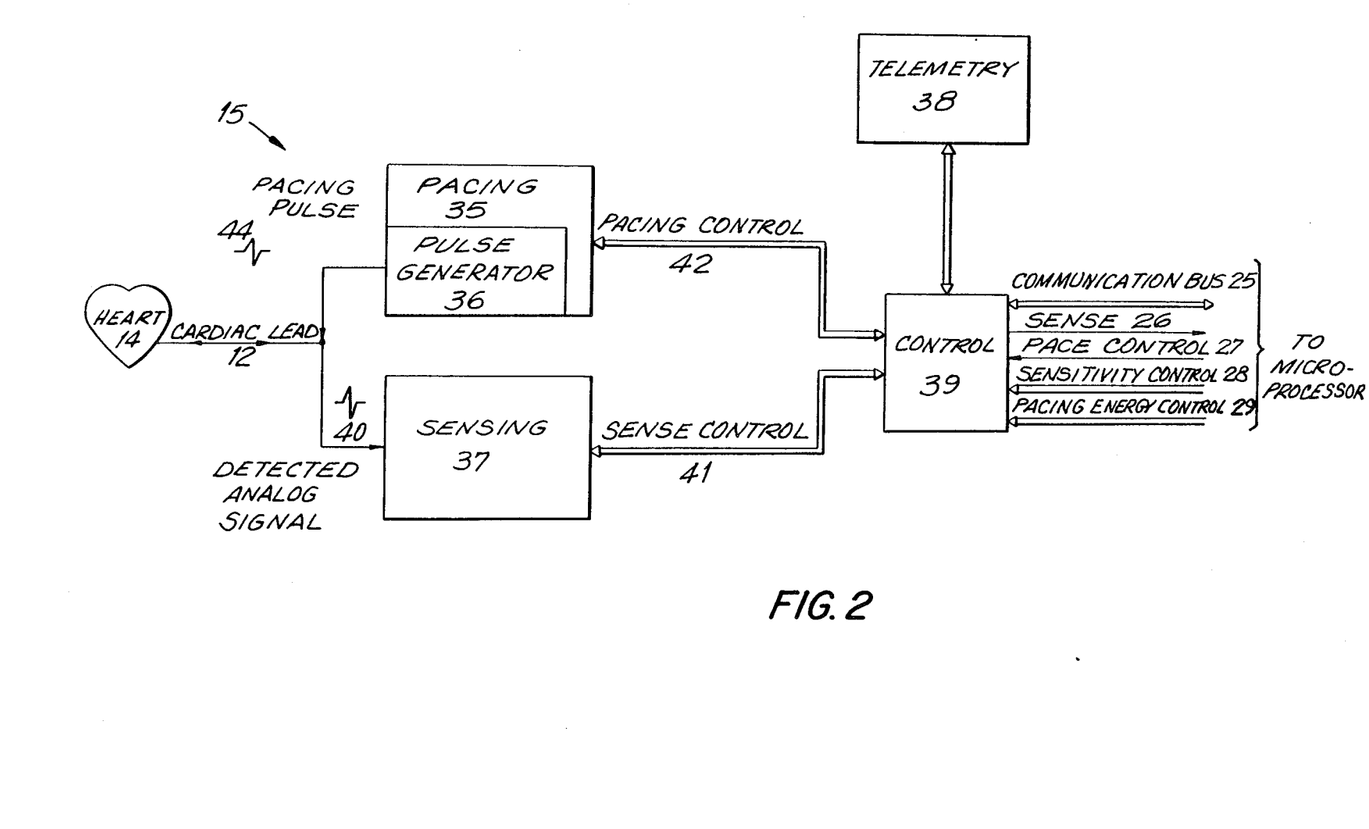
FIG. 2 is a block diagram of the pacemaker of FIG. 1.

Referring to FIG. 2, pacemaker 15 comprises pacing circuit 35 which includes a pacing pulse generator 36, sensing circuit 37, and telemetry circuit 38. In addition, there is a control block 39 which includes an interface to microprocessor 16.

In operation, sensing circuit 37 detects analog signals 40 from the heart 14 and converts the detected signals to digital signals. Furthermore, sensing circuit 37 receives an input sense control signal (which determines the sensitivity of the detection circuits in sensing circuit 37) by way of a sense control bus 41 from control block 39. A change in this sensitivity will affect the voltage deviation required at the sensing electrode for a sense to be registered. The operation of the logic which changes the sensitivity is described in more detail in the co-pending patent application Ser. No. 187,797 entitled "Apparatus and Method for Controlling Multiple Sensitivities in Antitachyarrhythmia Device", of Richard Grevis and Norma Louise Gilli, assigned to the same assignee as that of the present invention.

Pacing circuit 35 also receives inputs from control block 39 including a pace control and a pacing energy control by way of pacing control bus 42 which carries the signals on pace control line 27 and pacing energy control bus 29. The pace control determines the type of pacing to occur while the magnitude of the pulse energy is determined by the pacing energy control. Pacing circuit 35 causes pulse generator 36 to generate the pacing pulse 44 which is delivered to the patient's heart 14 by means of cardiac lead 12.

Telemetry circuit 38 provides a bi-directional link between control block 39 of pacemaker 15 and an external device such as a programmer. It allows data such as the operating parameters to be read from or altered in the implanted pulse module 11.

Figure 3:
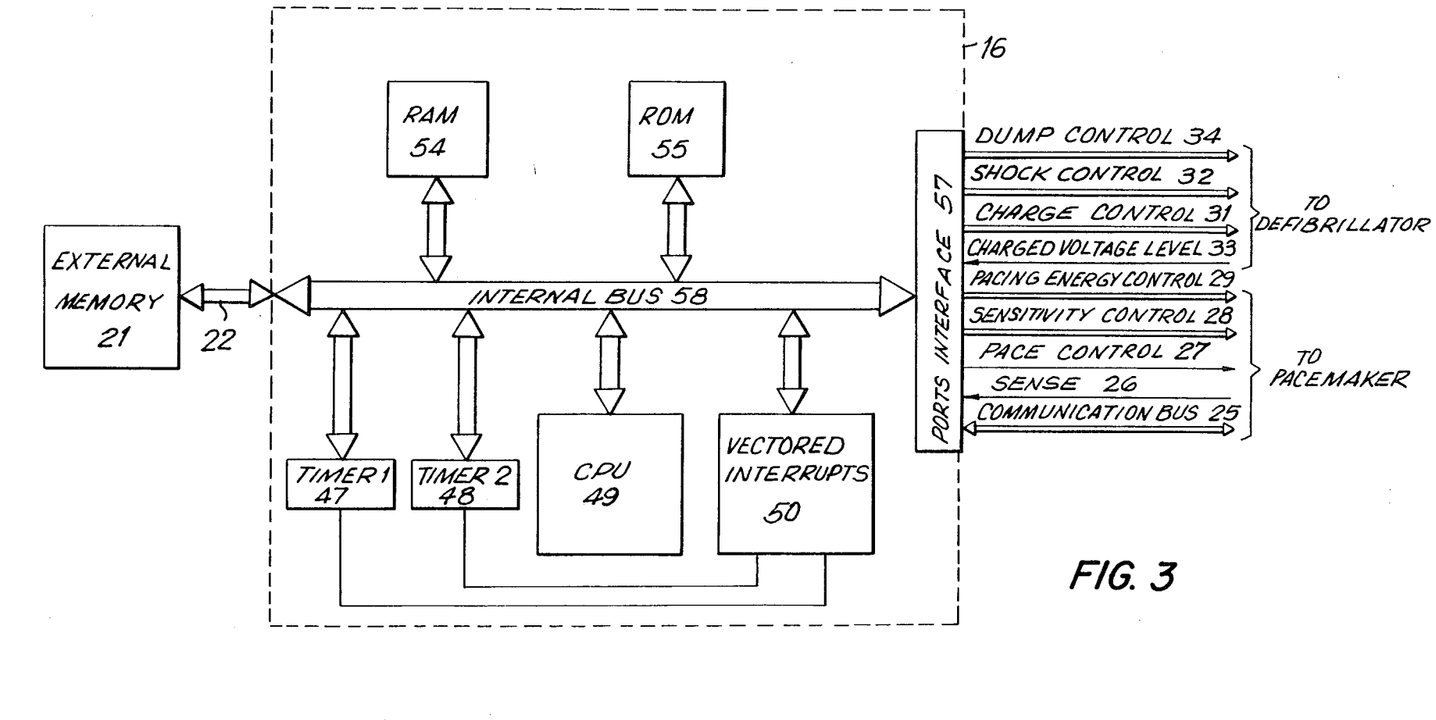
FIG. 3 is a block diagram of the microprocessor of FIG. 1.

Referring to FIG. 3, microprocessor 16 comprises two 16-bit timers 47 and 48, CPU 49, vectored interrupt block 50, RAM 54, ROM 55, ports interface 57 and an internal communications bus 58. RAM 54 acts as a scratch pad memory during execution of the various programs stored in ROM 55 and used by microprocessor 16. These programs include system supervisory programs, detection algorithms, and programming implementing the logic flow diagram of FIG. 4, as well as storage programs for storing, in external memory 21, data concerning the functioning of module 11 and the electrogram provided by cardiac lead 12. Timers 47 and 48 and associated control software implement some timing functions required by microprocessor 16 without resort entirely to software, thus reducing computational loads on and power dissipation by CPU 49.

Signals received from telemetry circuit 38 permit an external programmer (not shown) to change the operating parameters of pacemaker 15 by supplying appropriate signals to control block 39. Communications bus 25 serves to provide signals indicative of such control to microprocessor 16. Thus, it is also possible for an external programmer to control operation of defibrillator 17 by means of signals provided to microprocessor 16.

Appropriate telemetry commands may cause telemetry circuit 38 to transmit data to the external programmer. Data stored is read out, by microprocessor 16, on to communications bus 25, through control block 39 in pacemaker 15, and into control block 38 for transmission to the external programmer by a transmitter in telemetry circuit 38.

Microprocessor 16 receives various status and/or control inputs from pacemaker 15 and defibrillator 17. During normal pacer operations the input signal to pacemaker 15 is a sense signal on sense line 26 which is used by microprocessor 16 to perform operations such as arrhythmia detection. Microprocessor 16 produces outputs such as the pace control on pace control line 27 which determines the type of pacing to take place. Other pacemaker control outputs generated by microprocessor 16 include a pacing energy control signal on pacing energy control bus 29 which determines the magnitude of the pulse energy, and a sensitivity control signal on sensitivity control bus 28, which determines the sensitivity setting of the sensing circuit.

Microprocessor 16 provides to defibrillator 17 a shock control signal on shock control line 32 which indicates that a shock is to be delivered to the patient, a dump control signal on dump control line 34 which indicates that a shock is to be dumped at an internal load within defibrillator 17, and a charge control signal on charge control bus 31 which determines the voltage level of the shock to be delivered. Charge voltage level line 30 provides a digital signal representative of charge voltage from an analog to digital converter within defibrillator 17, thus providing a feedback loop which assures that a shock of proper energy level is delivered by defibrillator 17.

Figure 4:
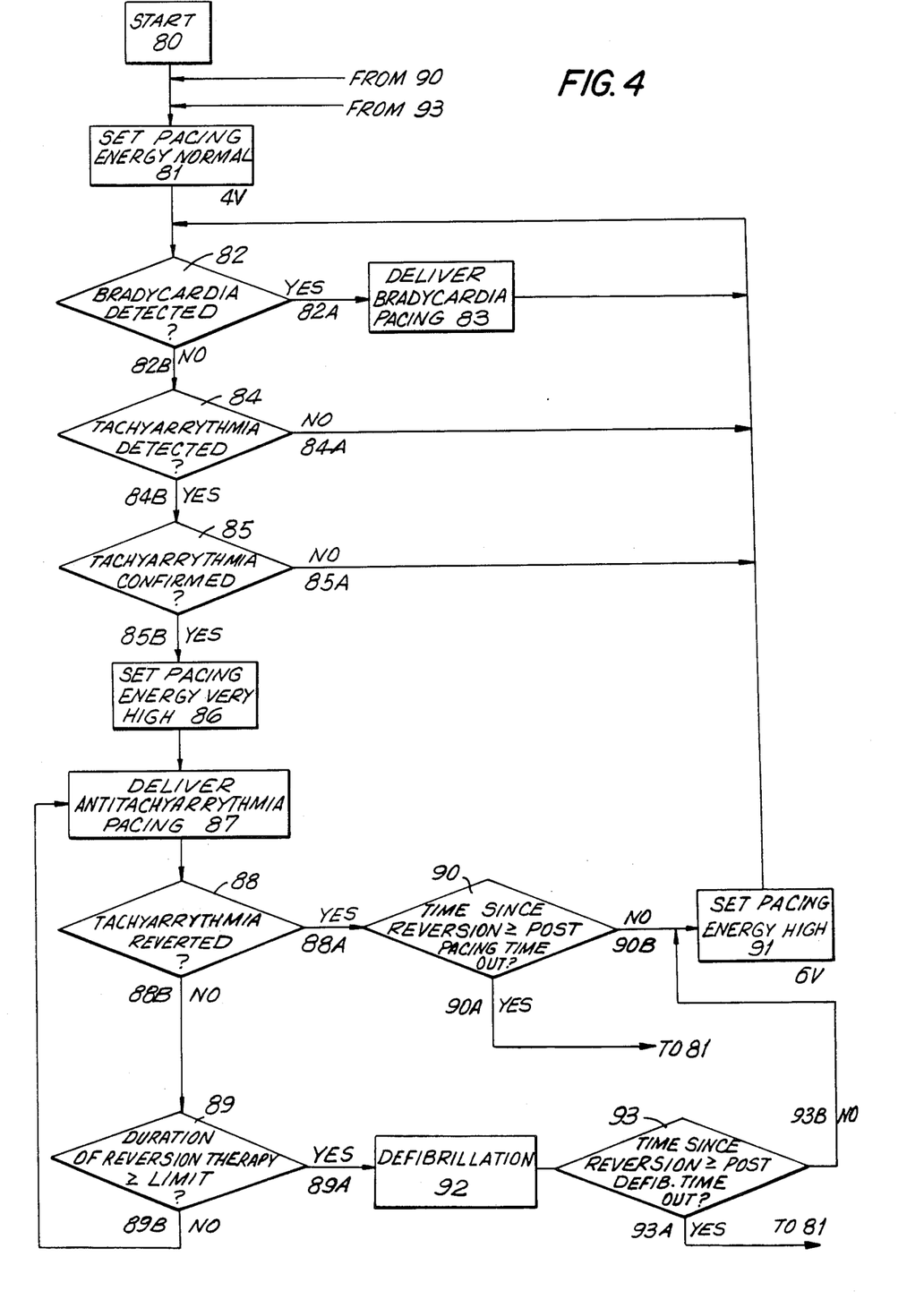
FIG. 4 is a logic flow diagram of the software executed by the microprocessor of FIG. 3 in accordance with the invention.

FIG. 4 is a logic diagram of the microprocessor flow control for changing pulse energies. The start is shown at 80, and at 81 the pacing energy is set to the normal value corresponding to 4 volts. At 82 a determination is made as to whether a bradycardia condition exists. If it does, then bradycardia pacing is delivered at normal pacing energy at 83.

If there is no bradycardia condition as shown at 82B, then branching occurs based on whether or not there is a tachyarrhythmia condition, as shown at 84. If there is no detection of a tachyarrhythmia condition as shown at 84A, then the program loops back through 82. If a tachyarrhythmia condition is detected at 84 as shown at 84B, then a confirmation of the tachyarrhythmia is given at 85. If a tachyarrhythmia condition is not confirmed as shown at 85A, then the program loops back to 82. If a tachyarrhythmia condition is confirmed, as shown at 85B, then the pacing energy is set to the very high level corresponding to 8 volts as shown at 86.

Antitachyarrhythmia therapy is then delivered to the patient as shown at 87. A determination is made at 88 as to whether or not the tachyarrhythmia has been reverted. If the tachyarrhythmia condition has not been reverted, as shown at 88B, then further antitachyarrhythmia therapy is delivered at 87. The therapy continues until reversion takes place at 88A, or for a given limited time as determined at 89 and as more fully explained below.

Reversion of a tachyarrhythmia at 88A starts a post-pacing timer at 90. As long as the time elapsed from reversion does not exceed a predetermined time interval, the pacing energy is set to the high level (corresponding to 6 volts) at 91 and it will remain at that high level until the expiration of the post-pacing timeout period at 90. The post-pacing timeout is a programmed period of time following antitachyarrhythmia therapy (in this case pacing) where the pulse energy is set at the high level in order to prevent a loss of capture due to the high probability of the heart being in a traumatic state. Programming may be performed by the physician either just prior to implantation, or changed after implantation through telemetry circuit 38.

If the pacing energy is high and the post-pacing timeout period is exceeded as shown at 90A, the command is given to set the pacing energy to the normal value corresponding to 4 volts at 81. If the time since tachyarrhythmia reversion has not exceeded the post-pacing timeout period, or if the pacing energy has been set (at 81) to the normal 4 volt value following the expiration of the post-pacing timeout period as shown at 90A, then at 82 branching occurs based on whether or not bradycardia has been detected. If a bradycardia condition is detected as shown at 82A, then bradycardia pacing is delivered as shown at 83. The pacing pulse energy will be either at the level corresponding to 6 volts (high) if the post-pacing timeout period has not expired, or at the level corresponding to 4 volts if the post-pacing timeout period has expired.

In any event, following reversion of the tachyarrhythmia condition, if post-pacing timeout has not occurred, at 90B the pacing energy is set to the high level of 6 volts, as shown at 91, and the loop passes back to 82. If the post-pacing timeout has occurred, at 90A branching to 81 occurs and the pacing energy is set to normal.

If there has been no indication of reversion at 88 and the time limit set at 89 for the duration of reversion therapy is exceeded, branching occurs to 89A and defibrillation is applied at 92. A post-defibrillation timer at 93 is reset, and the pacing energy is then set to the high level corresponding to 6 volts at 91. The program then loops back to 82. If the post-therapy (in this case, post-defibrillation) timeout has occurred, at 93A branching to 81 occurs and the pacing energy is set to normal.

In FIG. 4, the timeouts for high energy pacing may be different time intervals (as programmed into or fixed by the timers 90 and 93) depending upon whether antitachycardia has been reverted at 88 or defibrillation has occurred at 92. It is possible to implement a system wherein the same programmable timer is used in both cases, by, for example, eliminating timer 93 and connecting the output of block 92 as an additional input to timer 90, which could then be called, generally, a post-therapy timer. In that case, the timeout interval would be programmed (or fixed) to be the same after high energy pacing or defibrillation.

It is also desirable that bradycardia support pacing be inhibited for programmable periods of time after antitachycardia pacing or defibrillation which reverts a tachyarrhythmia so as to avoid any pro-arrhythmic effect. The use of such a delay is described in copending U.S. patent application Ser. No. 187,797 entitled "Apparatus and Method for Controlling Multiple Sensitivities in Antitachyarrhythmia Device", of Richard Grevis and Norma Louise Gilli, assigned to the same assignee as that of the present invention.

The time limit for the application of antitachyarrhythmia therapy at 87, determined by 89, is of importance. In this regard, reference is made to co-pending U.S. patent application Ser. No. 075,629 of Richard Grevis and Loraine Holley, filed July 20, 1987 and entitled "Apparatus and Method for Therapy Adjustment in Implantable Cardioverter", assigned to the assignee of the present invention, and which is incorporated herein by reference. In this application, the time limit for application of a shock is determined in accordance with the haemodynamic condition of the patient.

Figure 5:
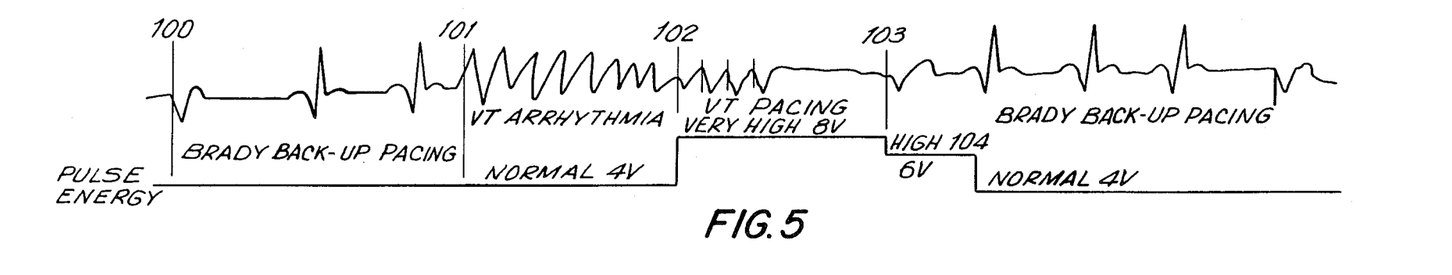
FIG. 5 is an ECG trace outlining the changing energy of pacing pulses in response to various cardiac conditions and therapies in an antitachyarrhythmia device.

Referring to FIG. 5 bradycardia back-up pacing is given at 100. The pulse energy is the "normal" bradycardia pacing energy of 4 volts. The bradycardia pacing energy is used for bradycardia support pacing in general and is programmed to a low energy sufficient to maintain capture. At 101, a VT arrhythmia is shown on the ECG. The therapy given at 102 in this instance is VT pacing and takes place at the "very high" pulse energy corresponding to 8 volts. These antitachyarrhythmia pacing pulses are delivered at a programmable energy (in this case corresponding to 8 volts) and are set independently of the bradycardia support pacing energies. Both the amplitude and the pulse width may be independently programmed. It is beneficial to set the antitachyarrhythmia pacing emerges to a high value to be assured of capture during a VT episode. Thus at 102, there is an increase in pulse energy associated with an increase from the normal 4 volts to the very high 8 volts. The VT pacing therapy has reverted the tachyarrhythmia as shown at 103 on the ECG trace. At this time a high energy, known as the post antitachyarrhythmia pacing energy and corresponding to a voltage of 6 volts, is used for bradycardia support pacing pulses which are delivered immediately after antitachyarrhythmia therapy. These pulses have a lower energy than the antitachyarrhythmia pacing pulses, but have a higher energy than the bradycardia pacing pulses in order to ensure capture in a heart that has just been traumatized by an episode of VT/VF and possibly shocks.

Thus, immediately upon the completion of antitachyarrhythmia therapy at 103, bradycardia support pacing pulses are delivered at the post antitachyarrhythmia therapy pacing energy (in this case 6 volt pulses). The bradycardia support pacing pulses are delivered at this higher energy (relative to the normal bradycardia support pacing pulses of 4 volts), until a programmable timeout period has expired. This is the period between 103 and 104. At 104, the subsequent bradycardia support pacing pulses are delivered at the normal bradycardia pacing energy corresponding to 4 volts.

Figure 6:
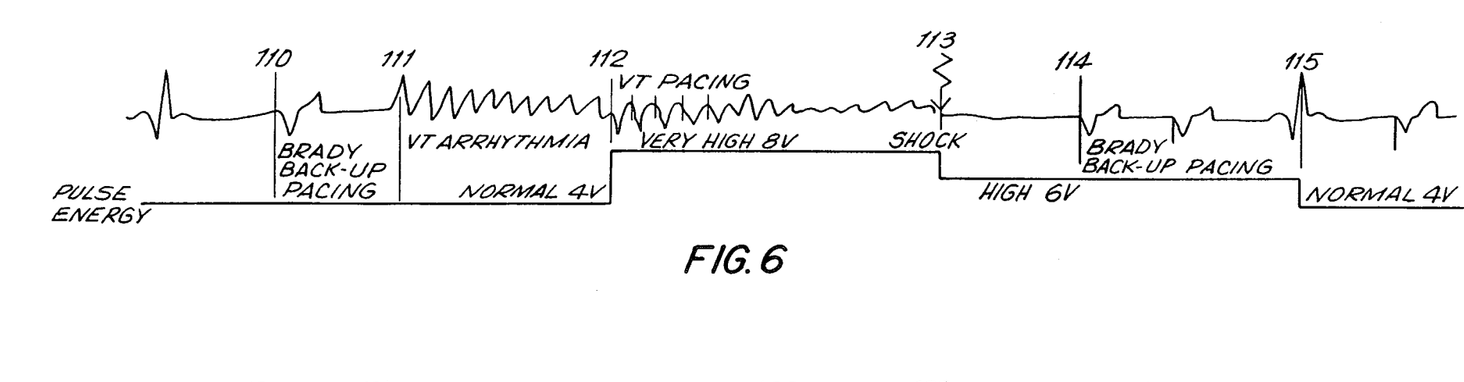
FIG. 6 is another ECG trace outlining the changing energy of pacing pulses in response to various cardiac conditions and therapies in an antitachyarrhythmia device.

Referring now to FIG. 6, there is depicted another ECG trace outlining the changing energy of pacing pulses in response to various cardiac conditions and therapies in an antitachyarrhythmia device. At 110, bradycardia support pacing is given at the normal bradycardia pacing energy corresponding to 4 volts. At 111, a VT arrhythmia has developed. Antitachyarrhythmia or VT pacing is given at 112 in an attempt to revert the tachyarrhythmia. These antitachyarrhythmia pacing pulses are delivered at a physician programmable energy and are set to a very high value in order to be assured of capture during the VT episode. In this instance the VT pacing energy is programmed at 8 volts. As shown in the ECG trace, the VT pacing has not proved to be successful in reverting the VT arrhythmia and thus the device performs a defibrillation shock at 113. As shown, the defibrillation shock has succeeded in reverting the VT arrhythmia and the device then performs post shock bradycardia support pacing at 114. The post antitachyarrhythmia therapy pacing energy is now used for the bradycardia support pacing pulses which are delivered immediately after the antitachyarrhythmia therapy, or as in this instance, defibrillation shock therapy. These pulses are programmed in this embodiment at 6 volts and have a higher energy than the normal bradycardia support pacing energy pulses of 4 volts to ensure capture in a heart which has just been traumatized by a defibrillation shock. At 115, the post antitachyarrhythmia pacing energy (6 volts) changes to the normal bradycardia support pacing energy (4 volts).

Figure 7:
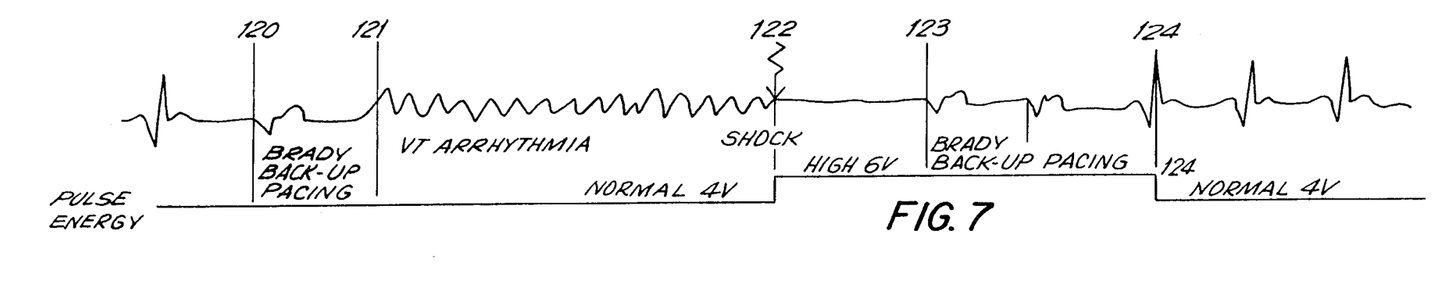
FIG. 7 is a further ECG trace outlining the changing energy of pacing pulses in response to various cardiac conditions and therapies in an antitachyarrhythmia device.

Referring now to FIG. 7, there is depicted a further ECG trace outlining the changing energy of pacing pulses in response to various cardiac conditions and therapies in an antitachyarrhythmia device. Bradycardia support pacing is shown at 120. These pacing pulses are delivered at the normal bradycardia pacing energy corresponding to 4 volts. A VT arrhythmia is shown to have developed at 121. At 122, defibrillation shock therapy is applied. The defibrillation shock therapy has been successful in reverting the VT arrhythmia. At this stage the pulse energy is set to correspond to 6 volts which is the higher energy level post antitachyarrhythmia pacing energy. These pacing pulses are delivered at the higher energy until the physician programmable timeout period has expired. This is shown at 124 on the ECG trace where there is a change from the post-shock pacing energy of 6 volts to the normal bradycardia pacing energy of 4 volts.

This invention applies to antitachyarrhythmia devices capable of delivering one or more cardioversion or defibrillation shocks as well as to devices which deliver antitachycardia pacing pulses alone or in combination with cardioversion or defibrillation shocks. The antitachycardia pacing may be delivered to the atrium, the ventricle, or to both the atrium and the ventricle.

It will be understood that various other implementations of the invention are contemplated. For example, although a microprocessor is used, the operations of FIG. 4 may be implemented using hard-wired logic rather than software, as the distinction between hardware and software has become less significant. In general, engineering judgment, including considerations of conserving energy so as to prolong battery life, is exercised in deciding on a particular implementation of the invention for a given application.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

I claim:

1. An apparatus for treating cardiac arrhythmias comprising:
   bradycardia pulse supplying means for supplying bradycardia pacing pulses at an energy level:
   detecting means for detecting a tachycardia;
   antitachycardia therapy means responsive to said detecting means for supplying antitachycardia therapy to revert said tachycardia; and
   energy level setting means responsive to said detecting means for setting said energy level of said bradycardia pacing pulses, said energy level setting means setting said energy level to a first discrete energy level, said energy level setting means setting said energy level to a second discrete energy level for bradycardia pacing after reversion of a tachycardia, said second level being higher than said first level.

2. The apparatus of claim 1, further comprising timing means for causing said energy level setting means to set the energy level of said bradycardia pacing pulses at said second level for a predetermined period of time.

3. The apparatus of claim 2, further comprising means for specifying said period of time as a fixed time interval.

4. The apparatus of claim 2, further comprising programming means for programming said predetermined period of time.

5. The apparatus of claim 2, wherein after said predetermined period of time said timing means causes said energy level setting means to deliver said bradycardia pacing pulses at said first energy level.

6. The apparatus of claim 2, wherein said timing means comprises a plurality of timers, each of said timers being responsive to the delivery of a respective antitachycardia therapy by said antitachycardia therapy means, each of said timers causing setting of an energy level by said energy level setting means at said second energy level for a period of time independently of others of said timers.

7. The apparatus of claim 1, wherein said antitachycardia therapy means includes at least one of:
   an antitachycardia pacing pulse generator,
   a cardioversion means, and
   a defibrillator.

8. The apparatus of claim 1, wherein said antitachycardia therapy means includes means for generating antitachycardia pacing pulses at an energy level, said energy level setting means setting said energy level of said antitachycardia pacing pulses at a third energy level, said third energy level being greater than said second energy level.

9. The apparatus of claim 8, wherein said energy level setting means includes at least one of pulse voltage selection means and pulse width selection means, said energy level being changed between said first discrete energy level, said second discrete energy level and said third antitachycardia pacing pulses energy level by changing at least one of pulse voltage and pulse width.

10. The apparatus of claim 1, further comprising tachycardia confirmation means for confirming the presence of tachycardia, said antitachycardia therapy means being activated only after said tachycardia is confirmed by said tachycardia confirmation means.

11. The apparatus of claim 1, further comprsing ascertaining means for ascertaining whether said tachycardia has been reverted, said ascertaining means causing said antitachycardia therapy means to terminate said therapy when said tachycardia has been reverted.

12. The apparatus of claim 11, wherein said antitachycardia therapy means includes:
   first therapy means for applying antitachycardia pacing; and
   second therapy means for applying defibrillation if said ascertaining means does not ascertain that reversion has occurred within a predetermined time interval.

13. The apparatus of claim 1, wherein said energy level setting means includes at least one of a pulse voltage selection means and a pulse width selection means, said energy level being changed between said first discrete energy level and said second discrete energy level by changing at least one of pulse voltage and pulse width.

14. A method for treating cardiac arrhythmias comprising the steps of:
   providing first bradycardia pacing pulses, said bradycardia pacing pulses being supplied at a first discrete energy level;
   detecting the presence of tachycardia;
   supplying antitachycardia therapy to revert said tachycardia; and
   delivering second bradycardia pacing pulses, after reversion of said tachycardia, said second bradycardia pacing pulses being of a second discrete energy level, said second discrete energy level being greater than said first energy level.

15. The method of claim 14, wherein said bradycardia pacing pulses are delivered at said second energy level for a predetermined period of time.

16. The method of claim 15, wherein after said predetermined period of time, said bradycardia pacing pulses are delivered at said first energy level.

17. The method of claim 15, wherein said antitachycardia therapy is at least one of a plurality of treatments, and for each of said treatments, said predetermined time is determined independently of other of said treatments.

18. The method of claim 14, further comprising the step of fixing said predetermined period of time.

19. The method of claim 14, further comprising the step of programming said predetermined period of time.

20. The method of claim 14, wherein said antitachycardia therapy is one of antitachycardia pacing, cardioversion and defibrillation.

21. The method of claim 14, wherein said antitachycardia therapy includes at least one pulse at a third energy level, said third energy level being greater than said second energy level.

22. The method of claim 21, wherein energy level is changed among said first energy level, said second energy level and said third energy level, by changing at least one of pulse voltage and pulse width.

23. The method of claim 14, further comprising the step of confirming the presence of a tachycardia prior to supplying antitachycardia therapy.

24. The method of claim 14, further comprising the step of periodically ascertaining whether said tachyarrhythmia has been reverted, said antitachycardia therapy being terminated upon reversion of said tachycardia.

25. The method of claim 14, wherein said antitachycardia therapy is antitachycardia pacing.

26. The method of claim 14, wherein said antitachyarrhythmia therapy is initially antitachycardia pacing, said antitachycardia pacing being supplied for only a predetermined period of time, said antitachycardia therapy being changed to defibrillation after said predetermined period of time has elapsed.

27. The method of claim 14, wherein energy is changed from said first energy level to said second energy level by changing at least one of pulse voltage and pulse width.

28. An apparatus for treating cardiac arrhythmias comprising:
bradycardia pulse supplying means for supplying bradycardia pacing pulses at an energy level:
detecting means for detecting a tachycardia;
antitachycardia therapy pacing means responsive to said detecting means for supplying antitachycardia pacing therapy to revert said tachycardia; and
energy level setting means responsive to said detecting means for setting said energy level of said bradycardia pacing pulses, said energy level setting means setting said energy level to a first energy level for bradycardia pacing, said energy level setting means setting said energy level to a second energy level for bradycardia pacing after reversion of a tachycardia, said second level being higher than said first level.

29. A method for treating cardiac arrhythmias comprising the steps of:
providing first bradycardia pacing pulses, said bradycardia pacing pulses being supplied at a first energy level;
detecting the presence of tachycardia;
supplying antitachycardia pacing therapy to revert said tachycardia; and
delivering second bradycardia pacing pulses, after reversion of said tachycardia, said second bradycardia pacing pulses being of a second energy level, said second energy level being greater than said first energy level.

* * * * *